United States Patent [19]

Bistrian

[11] Patent Number: 5,312,836
[45] Date of Patent: May 17, 1994

[54] SHORT CHAIN TRIGLYCERIDES

[75] Inventor: Bruce R. Bistrian, Ipswich, Mass.

[73] Assignee: New England Deaconess Hospital Corp., Boston, Mass.

[21] Appl. No.: 774,643

[22] Filed: Oct. 11, 1991

Related U.S. Application Data

[63] Continuation of Ser. No. 334,892, Apr. 7, 1989, abandoned.

[51] Int. Cl.$^5$ ............................................. C11C 3/02
[52] U.S. Cl. ......................................................... 554/224
[58] Field of Search ............................... 514/552, 549; 260/410.7; 554/224

[56] References Cited

U.S. PATENT DOCUMENTS

| | | | |
|---|---|---|---|
| 4,528,197 | 7/1985 | Blackburn et al. | 514/552 |
| 4,607,052 | 8/1986 | Mendy et al. | 514/547 |
| 4,703,062 | 10/1987 | Blackburn et al. | 514/582 |
| 4,810,726 | 3/1989 | Bistrian et al. | 514/552 |
| 4,847,296 | 7/1989 | Babayan et al. | 514/552 |

FOREIGN PATENT DOCUMENTS 0101046 2/1984 European Pat. Off. .

OTHER PUBLICATIONS

V. K. Babayan, 45 *J. Am. Oil Chem. Soc.* 1:23-25 (1967).
V. K. Babayan, 51 *J. Am. Oil Chem. Soc.* 6:260-264 (1974).
V. K. Babayan, 58 *J. Am. Oil Chem. Soc.* 1:49A-51A (1981).
Bach et al., *Am. J. Clin. Nutrit.* 36:950-962 (1982).
Koruda et al., Gastroenterology 95:715-720 (1988).
Journal of Dairy Science, vol. 47 No. 7, Jul. 1964, Champaign, Illinois U.S. pp. 727-732; R. G. Jensen et al.: "Intermolecular Specificity of Pancreatic Lipase and the Structural Analysis of Milk Triglycerides".

*Primary Examiner*—Jerome D. Goldberg
*Assistant Examiner*—Raymond J. Henley III

[57] ABSTRACT

A new class of synthetic triglycerides, those having at least one short-chain ($C_2$–$C_5$) fatty acid on a glycerol backbone, has been developed. These synthetic triglycerides (or structured lipids) are particularly useful in treating patients with intestinal problems.

3 Claims, No Drawings

SHORT CHAIN TRIGLYCERIDES

This application is a continuation, of application Ser. No. 07/334,892, filed Apr. 7, 1989 now abandoned.

BACKGROUND OF THE INVENTION

The present invention relates to parenteral nutrition and dietary supplements. More particularly, a new synthetic triglyceride family has been developed which provides numerous nutritional benefits and ease of breakdown when used either as a dietary supplement or for total parenteral nutrition. This new structured lipid or synthetic triglyceride has at least one short-chain (2-5 carbon backbone) fatty acid attached to a glycerol backbone.

Structured lipids have recently become a fertile testing ground in the field of parenteral nutrition. Although the ability to form structured lipids through procedures such as transesterification has been known for many years, only recently has an understanding of how the particular fats work in the body when released from a triglycerol backbone been sufficiently developed so as to lead to further exploration of structured lipids for nutritional uses. For example, the nutritional advantages of ω3 fatty acids, primarily in the form of fish oil, are now well documented. In like manner, the advantages of medium chain triglycerides ($C_8$-$C_{12}$) for parenteral nutrition, particularly with hypercatabolic patients, are now being explored. (See, e.g., U.S. Pat. No. 4,528,697.) However, not all structured lipids work alike, nor has it been possible to manufacture structured lipids with particular fatty acids on specific locations of the glycercol backbone until recently.

Although medium-chain fatty acids and long-chain fatty acids have been tested for the nutritional benefits for a long time, only recently has any thought been given to benefits of short-chain fatty acids (2-5 carbon backbone). These short-chain fatty acids are made in the colon from complex carbohydrates and fibrous polysaccarides by bacterial fermentation. These complex carbohydrates, such as pectin and glucans, when broken down to the short-chain fatty acids by the colonic flora, are the preferred fuels for the large and small intestinal cells, e.g., the intestinal mucosa. It has been suggested that short-chain fatty acids could provide nutrition for critically ill patients who cannot obtain sufficient fiber in the diet. This is particularly important since lack of enteric feeding of critically ill patients can lead to translocation of bacteria and endotoxin from the intestinal lumen into vascular system because of thinned intestinal mucosa. This problem is not ameliorated by use of parenteral nutrition since the intestinal cells are often deprived of their necessary nutrition.

However, the simple addition of short-chain fatty acids to parenteral nutrition does not appear to solve these problems. Short-chain fatty acids, when given as fatty acids, are potentially toxic. Moreover, since the short-chain fatty acids are much lower in calories than long-chain fatty acids, either a larger volume of the total parenteral nutrition diet must be used or the calorie content is decreased. Neither of these alternatives are good solutions for treating critically ill patients. In contrast, the synthetic triglyceride proposed herein can provide not only the short-chain fatty acids but also essential ω6 long-chain fatty acids as well as long-chain ω3 fatty acids.

Accordingly, an object of the invention is to provide a method of delivering short-chain fatty acids to the intestines as part of a total parenteral nutrition diet.

A further object of the invention is to provide a structured lipid containing short-chain fatty acids and medium or long-chain fatty acids.

Another object of the invention is to provide a structured lipid which, when fed enterally, enters the body through the portal system, partially bypassing the lymphatic system, while providing sufficient calories and delivery of the short-chain fatty acids to the intestinal mucosa.

These and other objects and features of the invention will be apparent from the following description and claims.

SUMMARY OF THE INVENTION

The present invention features a synthetic triglyceride and a method of treating patients who have difficulty absorbing material through the intestines, e.g., those patients who have had small bowel resections, pancreatic or biliary insufficiency, or other maladsorption syndrome, with the same family of synthetic triglycerides.

The synthetic triglyceride of the invention has the form

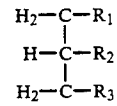

where $R_1$, $R_2$, and $R_3$ meet the following criteria:

A. $R_1$, $R_2$, and $R_3$ are fatty acids with at least one, but not all, being short-chain fatty acids having 2-5 carbons in the carbon backbone;

B. if $R_1$ and $R_3$ are the same short-chain fatty acid, $R_2$ is not a long-chain fatty acid having 14-22 carbon atoms in the carbon backbone; and C. those fatty acids which are not short-chain fatty acids are selected from the group consisting of long-chain ($C_{14}$-$C_{24}$) and medium-chain fatty acids ($C_6$-$C_{12}$).

Preferably, $R_2$ is either a short-chain fatty acid ($C_2$-$C_5$) or a medium-chain fatty acid having 6-12 carbon atoms in backbone. Most preferably, $R_2$ is the medium-chain fatty acid with $R_1$ and $R_3$ being short-chain fatty acids, most preferably $C_3$-$C_5$.

In a further embodiment of the invention, $R_1$ or $R_3$ are long-chain fatty acids, preferably ω3 fatty acids having 18-22 carbon atoms in the carbon backbone. Another of the preferred embodiments of the invention has a short-chain fatty acid, a medium-chain fatty acid, and an ω3 fatty acid on the same glycerol backbone.

As noted, the invention also features a method of treating patients who have difficulty absorbing nutrients through the intestines by use of a total enteral or parenteral nutrition diet having structured lipids with short-chain fatty acids as at least one of the residues being the primary lipid source in the diet. Patients in this state include both critically ill patients and those who have had small bowel resections or other forms of maladsorption syndrome. All of the members of the family of structured lipids of the invention may be used to treat these patients.

A further method of the invention is the treatment of hypercatabolic patients by administering a parenteral diet having structured lipids with short-chain fatty acids as at least one of the residues as the primary lipid source. Again, the structured lipids of the invention are the preferred triglycerides for use in this method.

DESCRIPTION OF THE INVENTION

The present invention features a new family or class of structured lipids or synthetic triglycerides and methods of treating critically ill or hypercatabolic patients with this class of the materials. These structured lipids provide better feeding of intestinal cells in the intestinal mucosa than current parenteral nutrition diets while providing the benefits of medium-chain and/or ω3 fatty acid additives.

The structured lipid of the invention may be formed by transesterification or any other lipid manufacturing process so long as the final product has at least one short-chain fatty acid ($C_2$–$C_5$) as one of the fatty acid residues on the triglyceride backbone. Short-chain fatty acids useful in the invention include acetic acid, propionic acid, butyric acid, and valeric acid, preferably in the straight chain rather than branch chain forms. When used as part of a parenteral nutrition diet, the bonds holding the short-chain fatty acids to the glycerol backbone are broken in the body, particularly at the intestine. Therefore, the short-chain fatty acids are released at the proper location for use as energy sources for the intestinal mucosa. The addition of these structured lipids to a parenteral nutrition diet provides the substantial equivalent of the fibers common in most diets, e.g., pectin and glucans, which are broken down by the intestinal flora to these same short-chain fatty acids. These short-chain fatty acids traverse the intestinal mucosa, providing nourishment to the intestinal cells. The use of this structured lipid ameliorates a problem common in conventional parenteral diets, that the body is able to function on the long-chain fatty acids used but the intestinal mucosa deteriorates because of lack of short-chain fatty acids. These synthetic triglycerides might even be helpful in the treatment, or prevention of colon cancer, providing some of the benefits of fiber in the diet.

Although the short-chain fatty acids may be located at any position on the triglycerol backbone, certain structured lipids within the broad family of the invention are preferred. If no other fatty calorie sources other than necessary amounts of linoleic acid are used in a total parenteral nutrition diet, synthetic triglycerides having ω3 fatty acids are preferred for use. The benefits of ω3 fatty acids in treatment of heart conditions, infection, and other conditions are well documented and new, positive applications of this family of fatty acids are being uncovered every day. Preferably, any long-chain fatty acids are in the $R_1$ or $R_3$ position on the triglycerides, leaving the $R_2$ position free for either short-chain fatty acid or medium-chain fatty acids. This $R_2$ position appears to have special properties, yielding the highest benefit if the proper residue for that position is selected judiciously.

As noted, many of the preferred structured lipids of the invention have medium-chain fatty acids on the triglyceride in addition to the short-chain fatty acids. If the structured lipids have just short-chain and medium-chain fatty acids, they can be transported entirely by the portal rather than the lymphatic system which improves speed of breakdown and insures better nutritional benefits. Therefore, one achieves benefits for the hypercatabolic patients because of the medium-chain fatty acids while feeding and sustaining the intestinal mucosa by the inclusion of the short-chain fatty acids, yielding an improved overall treatment of these patients. In fact, because of the problems associated with calorie intake in bowel resection or other patients with intestinal problems, the structured lipid of the invention provides a more improved treatment than has otherwise previously been available.

The structured lipid of the invention may be used as part of a total parenteral nutrition diet or as a supplement to other diets. As part of a total parenteral nutrition diet, 2–5% linoleic acid is necessary as are standard essential amino acids and minerals common in all lipid-based nutritional diets. If used merely as a supplement rather than the basic calorie source of a diet, the structured lipid of the invention will assist in upkeep of the intestinal mucosa without deleterious effects.

The structured lipid of the invention may be manufactured by any conventional means such as transesterification but the use of blocking groups which allow positioning of the residues at specific locations is preferred. Those skilled in the art are familiar with the variety of techniques useful for directing the residues to particular locations and they need not be set forth here in detail. It appears that the use of a medium-chain fatty acid in the two ($R_2$) position with short-chain fatty acids in the one ($R_1$) and three ($R_3$) positions leads to a most preferable triglyceride. As noted, the two position appears to be most important in directing the triglyceride to the proper pathway intake and ease of breakdown.

Those of ordinary skill in the art may discover other modifications or variations of the present invention. Such other modifications and variations are within the following claims.

What is claimed is:

1. A synthetic triglyceride of the form

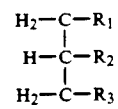

where $R_1$, $R_2$, and $R_3$ meet the following criteria:
  A. $R_1$, $R_2$, and $R_3$ are fatty acids with at least one, but not all, of $R_1$, $R_2$, and $R_3$ being a short-chain ($C_2$–$C_5$) fatty acid having 2–5 carbon atoms in the carbon backbone;
  B. $R_1$ is not the same fatty acid as $R_3$;
  C. the non-short-chain fatty acids are selected from the group consisting of long-chain ($C_{14}$–$C_{22}$) and medium-chain ($C_6$–$C_{12}$) fatty acids, with at least one of $R_1$, $R_2$, and $R_3$ being a medium-chain fatty acid; and
  D. $R_2$ is a medium-chain or short chain fatty acid.

2. The synthetic triglyceride of claim 1 wherein at least one of $R_1$ and $R_3$ is a long-chain fatty acid.

3. The synthetic triglyceride of claim 2 wherein at least one of said long-chain fatty acids comprises an ω3 fatty acid having 18–22 carbon atoms in the carbon backbone.